United States Patent [19]

Goralski

[11] 4,358,592

[45] Nov. 9, 1982

[54] GLAUCINE PHOSPHATE CHUNKY PRISMATIC CRYSTALS

[75] Inventor: Christian T. Goralski, Midland, Mich.

[73] Assignee: The Dow Chemical Company & Merrell Dow Pharmaceuticals Incorporated, Midland, Mich.

[21] Appl. No.: 230,244

[22] Filed: Feb. 2, 1981

Related U.S. Application Data

[63] Continuation-in-part of Ser. No. 115,976, Jan. 28, 1980, abandoned.

[51] Int. Cl.³ .......................................... C07D 221/18
[52] U.S. Cl. .................................................. 546/075
[58] Field of Search ................................... 546/66, 75

[56] References Cited

PUBLICATIONS

Chan et al., J. Chem. Soc. 753 (1966).
Cava et al., J. Org. Chem., 35, 175(1970).

*Primary Examiner*—David B. Springer
*Attorney, Agent, or Firm*—M. R. Johnson

[57] ABSTRACT

A crystalline form of d,l-glaucine phosphate is prepared by digesting d,l-glaucine phosphate with an alkanol. Glaucine phosphate has potent analgesic and antitussive properties, excellent flavor characteristics and stability properties and the new crystalline form has improved handling properties.

11 Claims, 10 Drawing Figures

FIG. 1 POLARIZED LIGHT 50X 100μm
FIG. 2 POLARIZED LIGHT 50X 100 μm
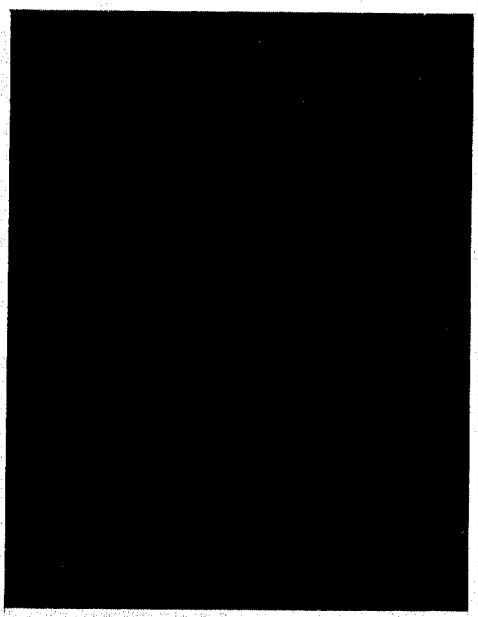
FIG. 3 SEM 200X 100 μm
FIG. 4 SEM 1000X 10 μm

GLAUCINE PHOSPHATE CHUNKY PRISMATIC CRYSTALS

This is a continuation-in-part of my copending application, Ser. No. 115,976, filed Jan. 28, 1980, abandoned.

CROSS REFERENCE TO RELATED APPLICATION

D,L-Glaucine phosphate, its preparation, and its use as an antitussive agent or analgesic agent are disclosed in a commonly-assigned copending application, Ser. No. 057,483, filed July 13, 1979, by Samuel S. M. Wang, now U.S. Pat. No. 4,315,010, issued Feb. 9, 1982, the disclosure of which is hereby incorporated by reference.

BACKGROUND OF THE INVENTION

Dextro-rotary glaucine or d-glaucine hydrobromide has been used as an antitussive agent. D-glaucine can be isolated from the yellow poppy. The racemate, d,l-glaucine can be synthesized from papaverine, following the procedure of Frank and Tietze, Angewandte Chemie (1967) pp 815–6, or Helm, Belgian Pat. No. 866,079, and the racemate can be resolved with d-tartaric acid as disclosed by the above mentioned Helm Belgian patent. A variety of other preparative procedures are also known. Chan and Maitland, J. Chem. Soc. (C) 1966, 753; and Cava, et al. J. Org. Chem. 35, 175 (1970). Separation of the isomers has been carried out by conventional procedures, such as using d- or l-tartaric acid to form the d- or l-bitartrate salts and separating the salts by fractional crystallization.

Glaucine has the structure

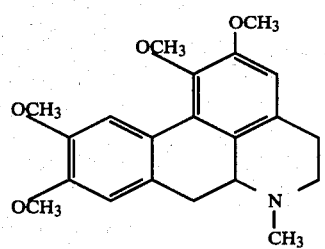

and is thus structurally somewhat related to other plant alkaloids such as codeine and aporphine. D,L-Glaucine, unlike codeine, forms a phosphate salt with about one and one-half molar proportions of phosphoric acid, as disclosed in the above-cited Wang application.

SUMMARY OF THE INVENTION

This invention is directed to a novel crystalline form of the phosphate salt of d,l-glaucine and to a method useful for preparing the same.

The d,l-glaucine phosphate salt has antitussive properties that are unexpectedly superior to the d-glaucine, and desirable solubility and high stability properties, unexpected flavor and palatability properties, analgesic activity, and low addictive potential. The novel crystalline d,l-glaucine phosphate of the invention has improved flowability, (including improved injectability in suspension form), greater bulk density, improved compression characteristics and other improved physical properties as compared to other crystalline forms. The novel crystals are highly uniform compact particles, of chunky prismatic habit. For brevity, the novel crystals can be referred to as "chunky prismatic crystals."

The term "habit," as employed herein, refers to the characteristic form of the crystals, as determined by the shapes and relative dimensions of the crystal faces. See, e.g., A Dictionary of Mining, Mineral and Related Terms, United States Department of the Interior, Bureau of Mines (1968); or Wells, A. F., Structural Inorganic Chemistry, Third Edition, Oxford (1962) pp 153–154. The term "prismatic," as used herein, refers to crystal elongation in one direction generally parallel to one of the crystal faces. As used herein, the term "prismatic" is not intended to require the morphology of a prism in the strict geometrical sense of a solid figure whose faces are parallelograms parallel to the axis and with two ends which are polygonal faces which are parallel to each other. Although a given crystalline particle of the invention can be viewed as comprising several geometric subunits which appear similar to prisms in a strict sense, the complete particle itself is prismatic in the sense of elongation, but not a single, simple prism in the strict geometric sense mentioned above.

The term "chunky" is employed herein to characterize a prismatic elongation which is considerably less pronounced than, for example, in a needle-like crystal. Thus, a "chunky prismatic" crystal has a relatively massive, block-like, or chunk-like, appearance, with the elongation amounting to only one or two, to on the order of four to six times the shorter dimensions.

The crystalline salt of the invention is prepared by digesting d,l-glaucine phosphate in a lower alkanol of one, two or three carbon atoms, for about four to eight hours, at a temperature of from about 50° C. to the boiling temperature optionally in the presence of phosphoric acid. The d,l-glaucine phosphate starting material can be glaucine phosphate prepared by the reaction of d,l-glaucine base with phosphoric acid and separated from the reaction mixture, with or without recrystallization. The digestion process of the invention can also be utilized to purify the novel crystalline form of d,l-glaucine phosphate, although this is not generally necessary.

BRIEF DESCRIPTION OF THE FIGURES

FIG. 1 is a photomicrograph of the chunky prismatic crystalline d,l-glaucine phosphate of the invention, made by polarized light microscopy with the polarizing filters uncrossed by 15°, and with a magnification of 50×.

FIG. 2 is a photomicrograph of typical needle d,l-glaucine phosphate crystals prepared by conventional recrystallization for comparison, using the same polarized light microscopy parameters and magnification employed in FIG. 1.

FIG. 3 is a scanning electron microscope (SEM) photomicrograph of the chunky prismatic d,l-glaucine phosphate crystals of the invention, with a 200× magnification.

FIG. 4 is an SEM photomicrograph of the chunky prismatic d,l-glaucine phosphate crystals of the invention, with a 1000× magnification.

DETAILED DESCRIPTION OF THE INVENTION

Figure 5:
FIGS. 5, 6, and 7 are each SEM photomicrographs of d,l-glaucine phosphate needles prepared by recrystallization, each at a magnification of 200×.

As is apparent from a comparison of FIGS. 1 and 2, the typical needle crystals of d,l-glaucine phosphate are much less uniform in size than the crystals of the invention. The typical crystals, as illustrated in FIG. 2, are long needles, which vary greatly in length and width, with a substantial percentage of crystals exceeding 100 micrometers ($100 \times 10^{-6}$ meters) in length, and a significant number of crystals exceeding 200 micrometers ($\mu$m) in length. In contrast, the crystals of the invention, as shown in FIG. 1, are of chunky prismatic habit, and are relatively uniform in size, with most crystals being about 100 $\mu$m or less in their longest dimension, and with no significant percentage (e.g. less than 1% by weight, and typically also less than 1% by number) of the crystals exceeding about 200 $\mu$m.

For convenience in describing the crystals, the crystal dimensions will be referred to as height (a), width (b) and length (c); the length (c) being taken as the greatest of the three dimensions, and height (a), being the smallest. The crystal dimensions of a, b and c will be expressed in terms of conventional orthogonal three dimensional axes, oriented so that the (c) axis corresponds to the longest dimension, and the (a) axis to the smallest. It is understood that the designation of a particular axis is an arbitrary convention employed for convenience in describing the crystals.

From the SEM photomicrographs of FIGS. 3-10, the differences in crystal morphology and dimensions between the chunky prismatic crystals of FIGS. 3 and 4 and the needles of FIGS. 5-10 are apparent.

The needle crystals are much longer than they are high or wide, i.e., (c) is much greater than (a) or (b). The needle crystals are relatively simple, with the a and b dimensions being generally uniform throughout the length (c) of individual crystals, and with well-defined planar faces along the (c) axis. The relative dimensions of the d,l-glaucine phosphate needles vary somewhat. In general the (a) and (b) dimensions are approximately equal, (b=1 to 2 a). In some cases, particularly the flat, wide crystals of FIGS. 7 and 10, the (b) dimension is on the order of 4 to 5 times (a), and larger in rare cases such as the very wide crystal below center in FIG. 9. The length (c) is many times the greatest height (a) (of the smallest dimension). In the vast majority of the needle crystals, the (c) measurement is 10 or more times the greatest a dimension, and in many of the needles (c) is equal to or greater than 30 times (a). Notable exceptions are two thick crystals to the center left of FIG. 5, with an apparent (c) on the order of 6 or 7 times (a), and small particles of debris from crystal fragmentation visible in FIGS. 7 and 10.

In contrast, the crystals of the invention, in the SEM photomicrographs of FIGS. 3 and 4, have the rather complex morphology of a multiplicity of joined prisms of different sizes. Individual crystals generally have the appearance of three, four, five or more generally parallelepipedal prisms fused together, with the interfacial junctions in single crystal particles being generally, but not always, in parallel planes and the particles resembling polycrystalline particles with generally parallel orientation of the individual crystallites. The crystalline particles thus have numerous planar faces, e.g., with as many as 8-10 or more planar faces being visible in an individual SEM photomicrograph of an individual chunky prismatic crystal. Also, the chunky prismatic crystals are much shorter than the needles, the typical (a) and (b) dimensions being approximately equal at their respective maxima, and the length (c) being only about one or two to about 4 or 5 times (a), with both (a) and (c) being compared at the points of greatest height and length.

The d,l-glaucine phosphate of chunky prismatic habit can be prepared by digestion of d,l-glaucine phosphate as described above. In the digestion process, d,l-glaucine phosphate (typically in the needle crystalline form) is mixed with a lower alkanol, preferably ethanol denatured with toluene, preferably in a ratio of about 6 to 12 liters of alkanol per kilogram of the salt. The alkanol can contain water, e.g. up to about 0.30 to 0.40 parts by volume of water per part by volume of alkanol. Sufficient lower alkanol is used to form a slurry, rather than dissolving all the salt. The digestion can be carried out in the presence or absence of phosphoric acid, and preferably phosphoric acid is employed in an amount up to the equivalent of about 0.3 parts by weight of 85 percent aqueous phosphoric acid per part by weight of d,l-glaucine phosphate (from 0 to 30 weight percent of aqueous $H_3PO_4$ per unit weight of the d,l-glaucine phosphate). Phosphoric acid is commercially available as the 85 percent solution in water, rather than in anhydrous form, and the amount of phosphoric acid is most conveniently expressed in terms of the 85 percent solution. In one preferred embodiment, 0.25 parts by weight of 85 percent $H_3PO_4$ are employed per part by weight of d,l-glaucine phosphate.

The slurry is then heated with stirring and digested for 4 to 8 hours, preferably at reflux temperatures and preferably under an inert gas blanket. The mixture is allowed to cool to ambient temperature, generally over a 12 to 20 hour period, during which time the prismatic crystals form. The product is recovered by conventional procedures such as filtration or centrifugation, and can be purified further, if desired, by washing and drying, or by a second digestion. Further purification is generally unnecessary.

The d,l-glaucine phosphate salt is a highly effective, orally active antitussive agent and also has analgesic activity when administered orally, combined with surprising palatability and desirable stability and solubility, and a useful freedom from undesired side effects, such as addictive properties. It can be administered at dosages of from about 0.1 to about 40 milligrams or more per kilograms (mg/kg) for antitussive effect, and from about 0.1 to about 60 mg/kg for analgesic use, preferably by oral administration. It is also active parenterally as an antitussive and analgesic, by intraperitoneal injection, for example.

D,L-Glaucine phosphate is generally effective at low dosages when administered orally as compared to parenteral dosages. For example, in antitussive evaluations in which codeine phosphate has an $ED_{50}$ of 10.9 mg/kg by intraperitoneal injection and an oral $ED_{50}$ of 86.6 mg/kg, the oral and intraperitoneal $ED_{50}$'s obtained with d,l-glaucine phosphate are quite similar, 17.8 and 17.3 mg/kg. In particular cases, the dosage to be administered can be ascertained by conventional range finding techniques, for example, by observing the antitussive activity produced at different dosage rates. The crystalline compound of chunky prismatic habit can be used in the same manner as the needle crystalline compound.

Dosage units adaptable to oral administration such as tablets, capsules, lozenges, elixirs, syrups and the like are preferred and the active glaucine phosphate compound can be formulated in conventional timed release capsule or tablet formulations.

In using the compounds of the invention, the active glaucine phosphate ingredient is preferably incorporated in a composition comprising a pharmaceutical carrier and from about 0.001 to about 95 percent by weight of the glaucine phosphate salt compound or a pharmacologically-acceptable salt thereof. The term "pharmaceutical carrier" refers to known pharmaceutical excipients useful in formulating pharmacologically-active compounds for internal administration to animals, and which are substantially non-toxic and non-sensitizing under conditions of use. The compositions can be prepared by known techniques for the preparation of tablets, capsules, cough drops, lozenges, troches, suppositories, solutions, elixirs, syrups, emulsions, dispersions, wettable and effervescent powders, sterile injectable compositions, and can contain suitable excipients known to be useful in the preparation of the particular type of composition desired. As with phosphates generally, liquid compositions should generally be substantially free of cations which form highly insoluble phosphate salts, to avoid undesired salt precipitation.

The chunky prismatic crystals of the invention have improved compression characteristics in comparison to the prior needle crystals, and are adapted to formation of compressed tablets of increased tablet hardness at lower compression pressures. Thus the crystals of the invention can form tablets which are better able to withstand handling, packaging and shipping without damage, using comparatively lower tablet compression pressure. For example, with 500 milligram tablets compressed with a concave 0.5 inch tablet punch and die in a hydraulic press at compression pressures of 3200 and 4200 pounds, the chunky prismatic crystals of the invention produced tablets with an average hardness about 1200 pounds or more greater than the tablet hardness obtained with the needle crystalline form of d,l-glaucine phosphate. In addition, the needle crystals tend to adhere to the tablet punch faces much more than the chunky prismatic crystals.

The chunky prismatic crystals of the invention are also adapted for the preparation of injectable suspensions in pharmaceutically-acceptable injectable liquid carriers which are not solvents for d,l-glaucine phosphate. Parenteral administration of the active compound can be necessary to control severe coughing in situations such as chlorine or ammonia over-exposure or veterinary conditions such as kennel cough. In such situations, coughing is often so frequent that oral administration of an antitussive is difficult or impossible. Injection of antitussive solutions provides effects of limited duration. Injection of a suspension of d,l-glaucine phosphate crystals of the invention in a non-solvent such as peanut oil, safflower oil or other pharmaceutically-acceptable oil carrier will provide sustained antitussive action of depot injection techniques. In suspension form, the crystals of the invention are adapted to flow through hypodermic syringe needles with much less tendency to plug or block the syringe needle. It can be seen from FIGS. 5-9, that the needle crystals tend to form clumps sufficiently large to impede flow through conventional injection syringes.

The compound may be administered in conjunction with other active ingredients or other antitussive or analgesic agents. Other active ingredients can include, for example, antihistamines, decongestants, expectorants, mucolytic agents, bronchodilators and antibacterial agents or local anesthetics. Combinations of this type are generally useful for treating coughing or pain in combination with other symptoms.

Particularly desirable compositions are those prepared in the form of dosage units, such as solid forms, including troches, lozenges, tablets, capsules, or measured volumes of liquid compositions, containing from about 0.1 milligram to about 20 to 30 to 40 milligrams of the glaucine salt per unit, for antitussive use and from about 0.1 milligram to about 30 to about 60 milligrams for analgesic use.

The invention is further illustrated in the following examples.

EXAMPLE 1

2.5971 Kilograms (5.95 mole) of d,l-glaucine hydrobromide, 10.0 liters of deionized water, and 3.5 liters of methylene chloride were mixed. The mixture was stirred rapidly, and 500 milliliters of 50 percent sodium hydroxide were slowly added. The sodium hydroxide was washed in with 100 milliliters of deionized water. After the addition was complete, the mixture was stirred for 15 minutes. The stirrer was then stopped and the mixture allowed to stand for 10 minutes to permit the layers to separate. The methylene chloride layer was drained off and stored. The aqueous layer was mixed with 3.5 liters of methylene chloride, and the mixture stirred rapidly for 15 minutes. The mixture was allowed to stand for 10 minutes to permit the layers to separate. The methylene chloride layer was drained off. An additional 200 milliliters of methylene chloride was added to the aqueous layer. The methylene chloride layer was drained off. The methylene chloride layers were combined and mixed with 3 liters of deionized water.

The resulting mixture was stirred rapidly for 15 minutes then allowed to stand for 15 minutes to permit the layers to separate. The methylene chloride layer was drained off and stored. This methylene chloride solution of d,l-glaucine base was then added to a well-stirred solution of 1.4235 kilograms (12.35 mole) of 85 percent phosphoric acid in 9.8 liters of toluene denatured, absolute ethanol. A heavy, white slurry formed. The slurry was stirred for 15 minutes, and then allowed to stand, under nitrogen, for about 14–16 hours. The stirrer was then started, and the slurry was slowly drained into 3 liter, sintered glass funnels. The solid which resulted was placed in large glass drying dishes and air dried, then vacuum dried at 50°–65° C. to give 2.902 kilograms (97.1 percent yield) of d,l-glaucine phosphate.

EXAMPLE 2

A 22 liter flask was charged with 1.500 kilograms of the d,l-glaucine phosphate from Example 1 and 15 liters of aqueous 80 percent toluene-denatured ethanol (20 percent water). The mixture was stirred and heated to reflux (78° C.) under nitrogen. The slurry was held at reflux for 5–6 hours, then allowed to cool to 22°–25° C. The resulting slurry was then slowly drained into 3 liter sintered glass funnels. The resulting solid was then air-dried. The solid was thoroughly washed with 3 liters of toluene denatured, absolute ethanol and air-dried again. The solid was then vacuum dried at 50°–65° C. to give 1.375 kilogram (91.7 percent recovery) of d,l-glaucine phosphate in the form of crystals of chunky prismatic habit.

By differential scanning calorimetry, the product showed a single peak, with a melting point of 253° C, H, N, found: 50.2, 5.97, 2.67; C, H, N calculated for $C_{21}H_{25}NO_4 \cdot 1.5H_3PO_4$: 50.2, 5.91, 2.79. Polarized light and SEM photomicrographs for this material are shown in FIGS. 1, 3 and 4.

EXAMPLE 3

Recrystallization of d,l-Glaucine Phosphate

A 22 liter flask was charged with 0.500 kilograms of d,l-glaucine phosphate and 10 liters of 80 percent toluene-denatured ethanol (20 percent water) were added. The mixture was heated to reflux (78° C.) and additional 80 percent ethanol was added until a total of 18.5 liters had been added. At this volume all of the material was in solution, except for 2 to 3 small white crystals which had not dissolved. 200 Milliliters of deionized water were added to the refluxing solution, which was then allowed to cool to 22° C. The resulting slurry was then slowly drained into a 3 liter sintered glass funnel. The resulting solid was then air-dried. The solid was thoroughly washed with one liter of toluene denatured, absolute ethanol and air-dried again. The solid was then vacuum dried at 50°–60° C. to give 0.386 kilogram (77.2 percent recovery) of d,l-glaucine phosphate, as needle shaped crystals.

Figure 8:
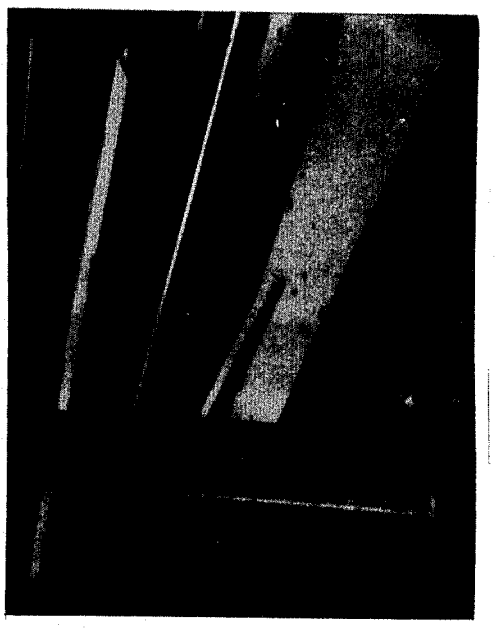
FIGS. 8, 9 and 10 are each SEM photomicrographs of d,l-glaucine phosphate needle crystals corresponding to FIGS. 5–7, with a magnification of 1000×.

By differential scanning calorimetry, the product showed a large peak, with a melting point of 253° C. and a single smaller peak at about 225°–226° C. C,H,N calculated for $C_{12}H_{25}NO_4 \cdot 1.5H_3PO_4$: 50.2, 5.91, 2.79. C,H,N found: 50.5, 5.93, 2.82. Polarized light photomicrographs and SEM photomicrographs of this product are illustrated in FIGS. 2, 5 and 8.

Figure 6:
Figure 9:
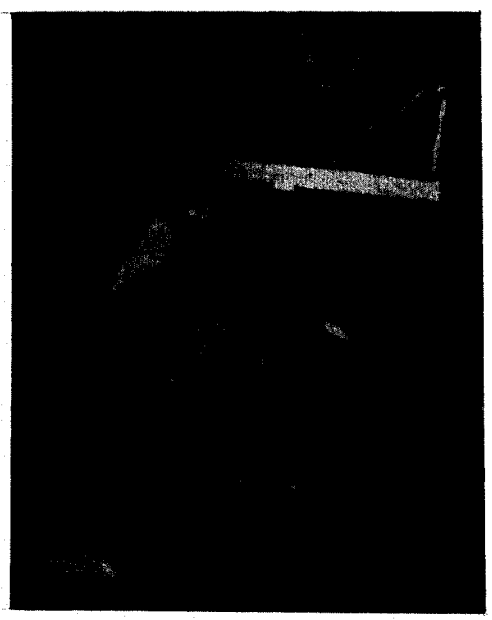

The SEM photomicrographs of FIGS. 6 and 9 are of d,l-glaucine phosphate recrystallized in a similar procedure on a smaller scale (approximately 10 grams).

Figure 7:
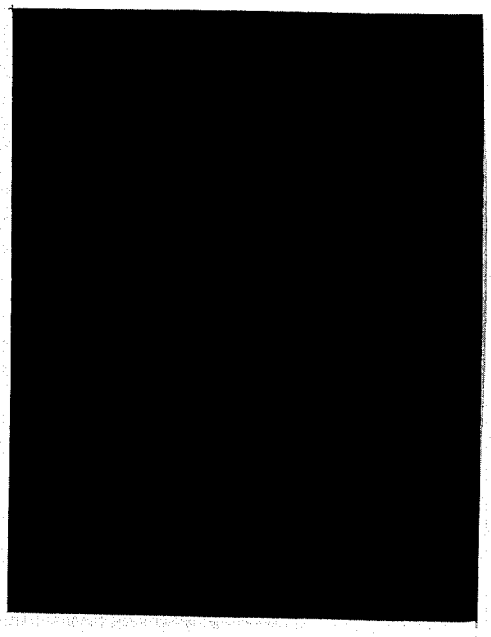
Figure 10:
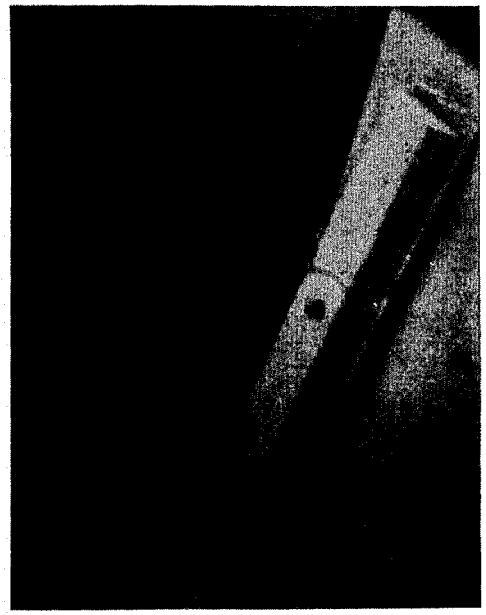

The SEM photomicrographs of FIGS. 7 and 10 are of d,l-glaucine phosphate recrystallized in a procedure in which the glaucine salt was dissolved in refluxing ethanol (approximately a 0.5 percent solution) and the solution was covered and allowed to cool to room temperature without agitation, then held for 48–72 hours before filtration.

EXAMPLE 4

Digestion of d,l-Glaucine Phosphate in the Presence of Phosphoric Acid

A 50 liter flask was boiled out with 8.0 liters of deionized water. The flask was charged with 4.0 liters of deionized water and 16.0 liters of toluene-denatured, absolute ethanol. The flask was then charged with 4.175 kilograms (kg) of crude d,l-glaucine phosphate. The flask was then charged with 4.0 liters of deionized water, 14.0 liters of toluene-denatured, absolute ethanol, and 1.045 kg of aqueous 85% phosphoric acid. The mixture was heated to reflux (approximately 78° C.) and held there for 6 hrs. The mixture was then allowed to cool slowly to room temperature. The solid was then filtered from the slurry in six approximately equal portions, and air dried. Each air-dried cake was washed twice with 0.70 liter of toluene-denatured, absolute ethanol. The solid was then vacuum dried at 50°–60° C. for 48 hours to give 3.691 kg of d,l-glaucine phosphate crystals of chunky prismatic habit (88.4% recovery, greater than 99 percent purity).

EXAMPLE 5

Tablets are prepared by blending 30 parts by weight of d,l-glaucine phosphate chunky prismatic crystals, 135 parts by weight of microcrystalline cellulose NF (National Formulary); 33 parts by weight of lactose, hydrous, USP, and 2 parts by weight of magnesium stearate NF, and compressing the mixture into 200 milligram tablets. Each tablet contains 30 milligrams of the active ingredient.

Tablets can also be prepared by blending 30 parts by weight of the crystals of the invention with 127.5 parts lactose, hydrous, USP, 8 parts methyl cellulose, USP, (15 centipoise), and 16 parts of starch NF; adding water (about 30 to 40 parts) to prepare a granulation, and screening and drying the granulation. The granulation is mixed with an additional 18 parts starch and 0.5 part of magnesium stearate, and the resultant mixture compressed into 200 milligram tablets in conventional tableting equipment.

What is claimed is:

1. Crystalline d,l-glaucine phosphate of chunky prismatic habit, having the morphology of at least three generally parallelepipedal prisms of different sizes fused together with the interfacial junctions being generally in parallel planes.

2. D,L-Glaucine phosphate, being in the form of chunky prismatic crystalline particles having a length of from about 1 to about 5 times the height thereof, said particles having a morphology resembling polycrystalline particles with generally parallel orientation of the individual crystallites.

3. D,L-Glaucine phosphate having the crystal morphology illustrated in FIGS. 3 and 4.

4. A process comprising:
(a) forming a slurry of d,l-glaucine phosphate in a lower alkanol;
(b) digesting the slurry at a digestion temperature of from about 50° C. to the boiling temperature;
(c) thereafter reducing the temperature of the slurry below the digestion temperature range; and
(d) separating crystalline d,l-glaucine phosphate having the crystal morphology illustrated in FIGS. 3 and 4 from the slurry.

5. Process of claim 4 wherein the lower alkanol is ethanol.

6. Process of claim 5 wherein the slurry is digested at the boiling temperature under reflux for at least about 4 hours.

7. Process of claim 6 wherein the digested slurry is cooled to a temperature of about 5° to about 30° C. over from 8 to about 20 hours.

8. Process of claim 5 wherein the digestion is carried out in the presence of phosphoric acid in an amount up to the equivalent of about 0.3 parts by weight of aqueous 85 percent phosphoric acid per part by weight of the d,l-glaucine phosphate.

9. Process of claim 8 wherein the phosphoric acid is employed in an amount equivalent to about 0.25 parts by weight aqueous 85 percent $H_3PO_4$ per part by weight of d,l-glaucine phosphate.

10. Process of claim 4 wherein the ethanol is aqueous ethanol containing about 20 percent water.

11. D,L-Glaucine phosphate having the crystal morphology illustrated in FIGS. 3 and 4 and prepared by a process consisting essentially of digesting a slurry of d,l-glaucine phosphate in a lower alkanol at a temperature from about 50° C. to the boiling temperature, thereafter reducing the temperature below the digestion temperature range, and separating the resulting D,L-glaucine phosphate product having said crystal morphology.

* * * * *

UNITED STATES PATENT AND TRADEMARK OFFICE
CERTIFICATE OF CORRECTION

PATENT NO. : 4,358,592
DATED : November 9, 1982
INVENTOR(S) : Christian T. Goralski It is certified that error appears in the above-identified patent and that said Letters Patent is hereby corrected as shown below:

On the title page item [73] should read:

Assignee:  --Merrell Dow Pharmaceuticals Inc.--.

Signed and Sealed this

Fourteenth Day of June 1983

[SEAL]

Attest:

DONALD J. QUIGG

Attesting Officer

Acting Commissioner of Patents and Trademarks